United States Patent [19]
Highe et al.

[11] Patent Number: 5,289,822
[45] Date of Patent: Mar. 1, 1994

[54] ELECTRODE FOR REDUCING THE SURFACE RESISTIVITY OF SKIN AND METHOD

[75] Inventors: Albert J. Highe, Redwood City; Mir A. Imran, Palo Alto, both of Calif.

[73] Assignee: Physiometrix, Inc., Sunnyvale, Calif.

[21] Appl. No.: 983,823

[22] Filed: Dec. 1, 1992

[51] Int. Cl.$^5$ .................................................. A61B 5/04
[52] U.S. Cl. ........................................ 128/640; 607/153; 252/511; 428/327
[58] Field of Search .......................... 128/639–641, 128/644, 798, 802–803; 428/327, 343–344, 350, 355–356; 252/511; 607/149, 152–153

[56] References Cited

U.S. PATENT DOCUMENTS

| | | | |
|---|---|---|---|
| 4,274,420 | 6/1981 | Hymes | 128/798 X |
| 4,367,745 | 1/1983 | Welage | 128/798 X |
| 4,406,827 | 9/1983 | Carim | 128/639 X |
| 4,524,087 | 6/1985 | Engel | 128/639 |
| 4,658,826 | 4/1987 | Weaver | 128/640 |
| 4,674,512 | 6/1987 | Rolf | 128/640 |
| 5,205,297 | 4/1993 | Montecaivo et al. | 128/641 X |

FOREIGN PATENT DOCUMENTS 1219642 3/1987 Canada.

OTHER PUBLICATIONS

Kerber, *External Defibrillation: New Technologies*, Annals of Emergency Medicine, Sep. 1984, pp. 794–797.
Aubry-Frize, et al., *Modelling of Thermal Patterns of Electrosurgical Dispersive Electrodes*, Medical & Biological Engineering & Computing, May 1986, pp. 311–316.
IEEE Transactions on Biomedical Engineering, vol. BME-29, No. 5, May 1982, pp. 381–389.

Primary Examiner—Angela D. Sykes
Attorney, Agent, or Firm—Flehr, Hohbach, Test, Albritton & Herbert

[57] ABSTRACT

Electrode adapted to be placed in contact with the skin of a patient for reducing the surface resistivity of the skin of the patient and comprising a member formed of a dry-conductive material and having an outer surface adapted to be placed in contact with the skin of the patient. A composition is disposed on at least a portion of the surface of the member. The composition as is the surface of a plurality of water-containing vesicles.

28 Claims, 2 Drawing Sheets

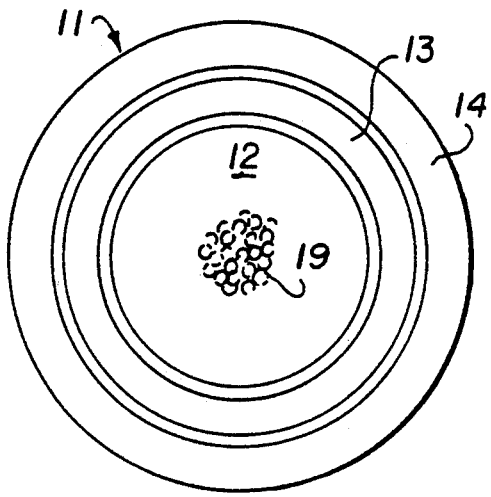
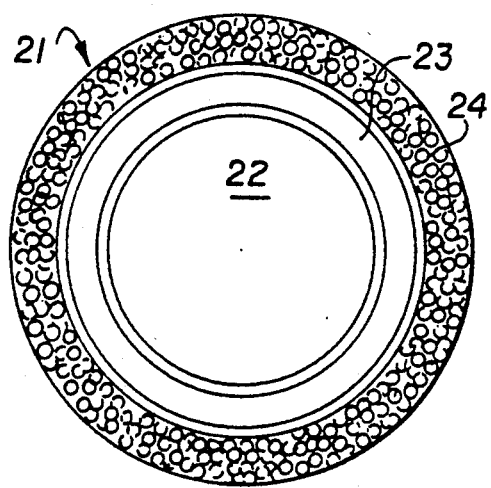
FIG.1    FIG.2
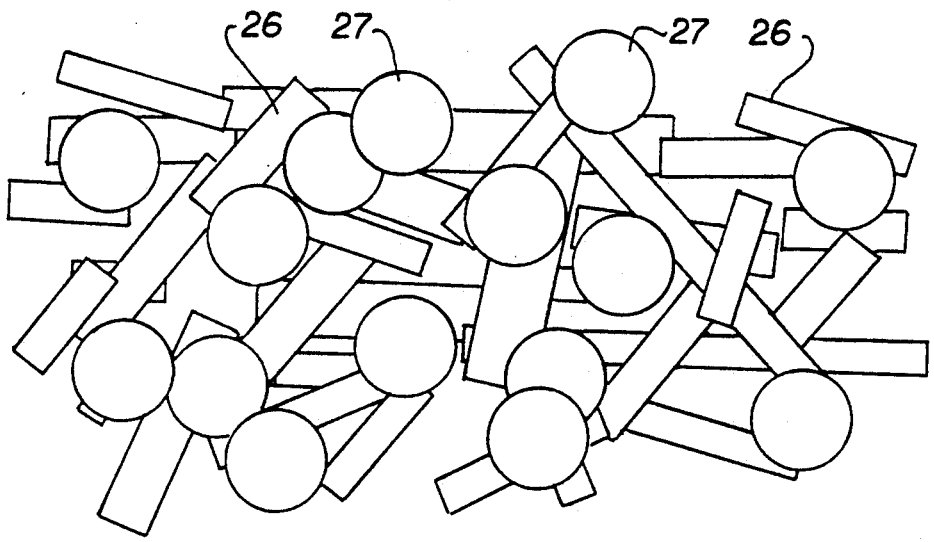
FIG.3

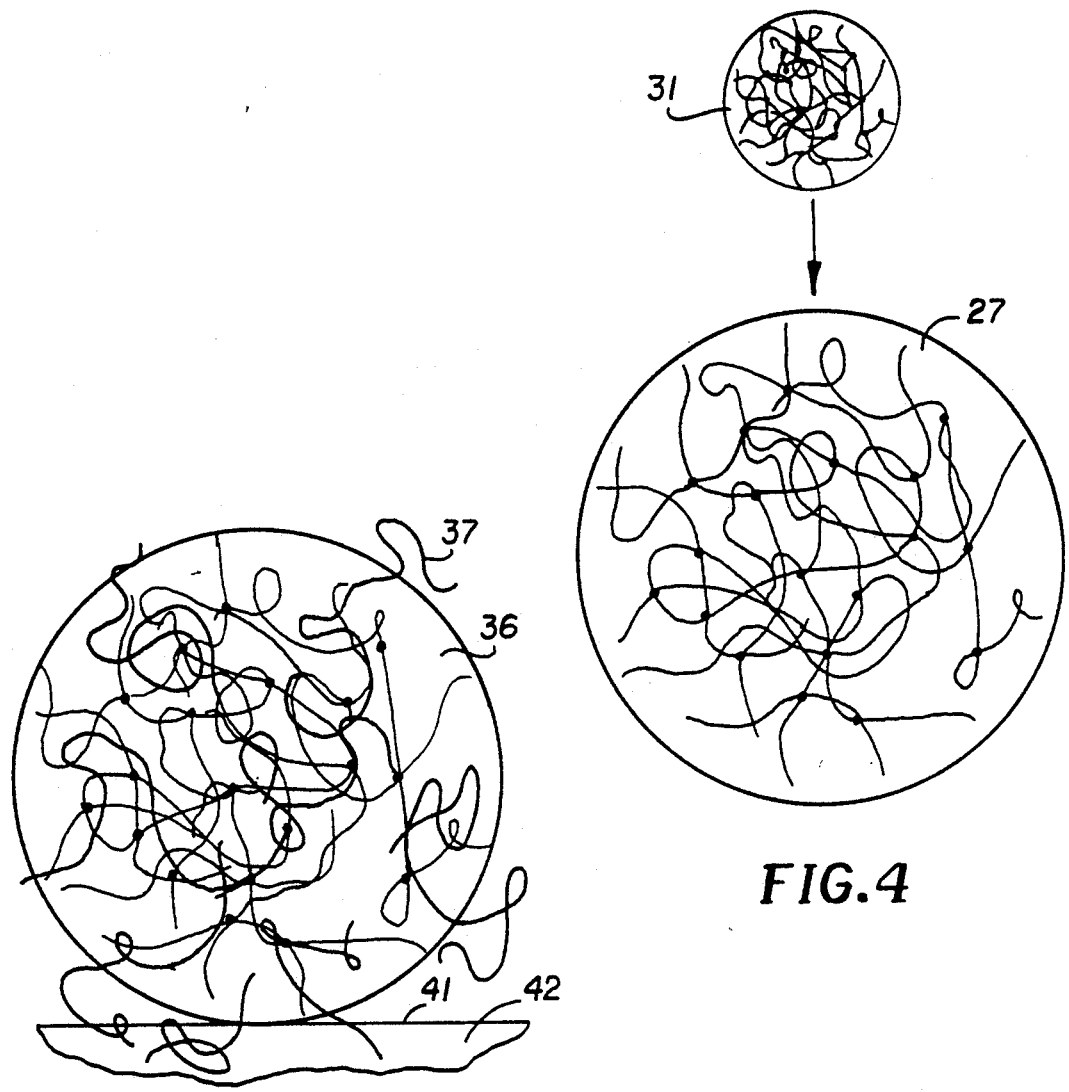
FIG.4
FIG.5
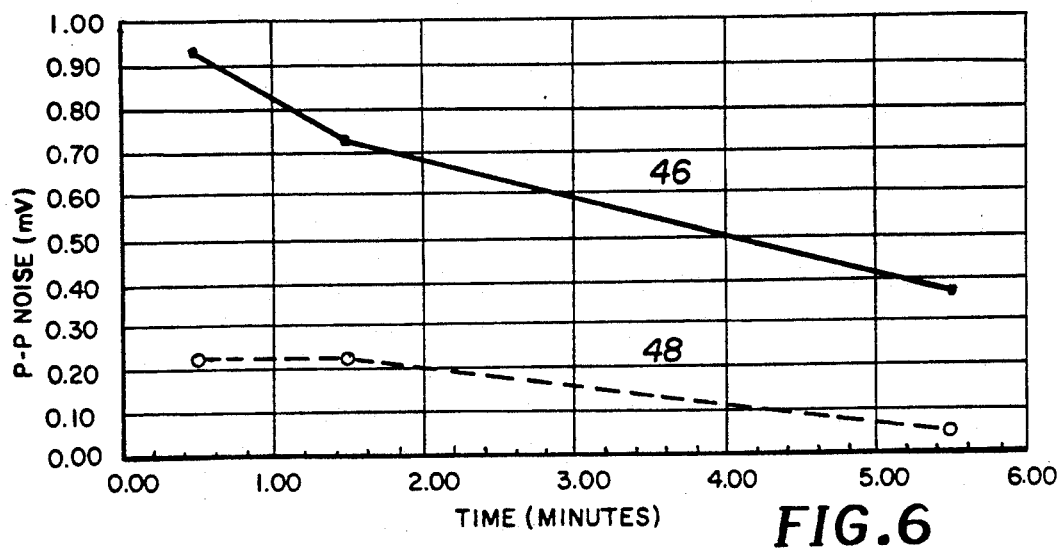
FIG.6

ELECTRODE FOR REDUCING THE SURFACE RESISTIVITY OF SKIN AND METHOD

BACKGROUND OF THE INVENTION

This invention relates to an electrode which is adapted to be placed in contact with the skin of the patient and for reducing the surface resistivity of the skin of the patient and method.

In the use of certain types of electrodes which are characterized as dry electrodes and which contain very little or no water such as polymer composites (polymers filled with a conductive filler). There is no water present to help moisturize the surface layer of the skin of the patient upon which the electrode is placed. It has been found that this lack of moisture is particularly important upon the initial application of the electrode to the skin until there is a natural build up of moisture in the skin of the patient which typically occurs after a period of time, as for example, four minutes or more. There is, therefore, a need for an improved electrode which has the capabilities of reducing the resistivity of the skin particularly immediately upon placing the electrode in contact with the skin.

In general, it is an object of the present invention to provide an electrode and a method which reduces the surface resistivity of the skin.

Another object of the invention is to provide an electrode and method of the above character which is particularly useful for dry-type electrodes.

Another object of the invention is to provide an electrode and method of the above character in which the surface of the electrode is treated.

Another object of the invention is to provide an electrode and method of the above character which involves a composition which can be readily applied to the surface of the electrode.

Another object of the invention is to provide an electrode and method of the above character in which the tackiness of the surface of the electrode is substantially unimpaired.

Another object of the invention is to provide an electrode and method of the above character in which the surface treatment does not have deleterious effects on the skin of the patient.

BRIEF DESCRIPTION OF THE DRAWINGS

Additional objects and features of the invention will appear from the following description in which the preferred embodiments are set forth in conjunction with the accompanying drawings.

FIG. 1 is a plan view of an electrode incorporating the present invention in which a treatment composition is applied to the center portion of the outer surface of the electrode.

FIG. 2 is a plan view of another electrode incorporating the present invention in which a surface treatment is applied to the outer perimeter of the outer surface of the electrode.

FIG. 3 is a greatly enlarged schematic illustration showing the manner in which the treatment composition is incorporated onto the surface of the electrode.

FIG. 4 is a schematic illustration showing the manner in which a bead is utilized in making the treatment composition of the present invention and how it is expanded to a vesicle utilized in the treatment composition.

FIG. 5 is a schematic illustration showing a vesicle such as shown in FIG. 4 to which a tackifier has been added to improve skin adhesion.

FIG. 6 is a graph showing coated and uncoated electrodes and showing the manner in which the treatment composition utilized for the surface of the electrode greatly reduces the resistivity of the skin during ECG measurements.

DETAILED DESCRIPTION OF THE PREFERRED EMBODIMENTS

In general, an electrode incorporating the present invention is adapted to be placed in contact with the skin of the patient for reducing the surface resistivity of the skin of the patient is comprised of a member formed of a dry conductive material having an outer surface adapted to be placed in contact with the skin of the patient. A paste-like composition covers at least a portion of the outer surface of the member. The paste-like composition is comprised of a plurality of water-containing vesicles which reduce the resistivity of the skin of the patient.

More in particular, an electrode 11 incorporating the present invention is shown in FIG. 1. It has a construction of the type described in co-pending application, Ser. No. 07/964,917 filed Oct. 22, 1991, and as described therein consists of a circular portion 12 and two concentric ring portions 13 and 14. The portions 12, 13 and 14 are formed of a material described in co-pending application, Ser. No. 07/745,863, filed on Aug. 16, 1991, as described therein as a polymer composite which has little or no water in the same and which also can be characterized as a conductive elastomer. The material is also described in the co-pending application, Ser. No. 07/793,858, filed on Nov. 18, 1991. The electrode 11 has an outer surface 16 which is provided by the surfaces of the circular portion 12 and the ring portions 13 and 14.

A surface treatment composition 19 incorporating the present invention is disposed on the outer surface 16 of the electrode 11 shown in FIG. 1. This surface treatment composition 19 is provided on the central portion of the circular portion 12. In the electrode 21 shown in FIG. 2 which is provided with a circular portion 22 and two concentric ring portions 23 and 24, the treatment composition 19 is provided on the portion of the outer surface 16 provided by the outer concentric ring 24. It should be appreciated that the treatment composition of the present invention can be provided on any part or a portion of the outer surface on the electrode and still accomplish the goals of the present invention.

The manner in which the treatment composition commingles with the outer surface of the electrode 11 or 21 is shown schematically in FIG. 3. The conductive elastomer which is utilized for the dry electrode material is shown in plan with a plurality of conductive elements 26 disposed therein in the form of silver-coated glass rods which are randomly oriented as shown and in which the treatment composition 19 of the present invention is shown dispersed therein in the form of water-containing vesicles 27 of the type hereinafter described. The vesicles 27 as hereinafter described are typically spherical. However it should be appreciated that other shapes can be used, as for example in the form of filaments having a diameter on the order of less than 100 microns. They are also randomly disposed on the surface of the electrode. As it can be seen, the vesicles 27 are not so large so that they interfere with the performance of the conductive elements 26 being able to come into contact with the skin of the patient. Thus, the conductive elements 26 have a diameter ranging from 15-25 microns and have lengths ranging from 10-500 microns with an average of 80-150 microns. In order to nestle among the conductive elements of this size, it is desirable that the vesicles 27 not have a size which is substantially greater than the size of the conducting elements. Thus, the size of the vesicles for such conducting elements should be less than 100 microns on the order of 40-50 microns in diameter. Vesicles of such a size nestle very well among the conducting elements 26 and do not prevent the conducting elements 26 from coming into contact with the skin. These vesicles 27 as hereinafter described are water-containing vesicles and serve to reduce skin resistivity as hereinafter described.

The water-containing vesicles 27, in accordance with the present invention, are manufactured by utilizing resin elements in the form of beads 31 which are commercially available. These beads 31 may be purchased from BioRad of Richmond, Calif. One resin bead found to be satisfactory is a crosslinked polyacrylamide bead which typically is comprised of hydrophilic-type polymers which have been crosslinked. The degree of crosslinking dictates the amount of swelling which will occur upon absorption of water without dissolving. Ion exchange resin beads can also be utilized. It is important that in all of these beads that some degree of crosslinking be provided to make it possible for the beads to absorb at least some water. In connection with the present invention, it is desirable that the beads absorb a substantial amount of water. For that reason, it is desirable to pick beads which have a lower degree of crosslinking, as for example from less than 10% crosslinking so that such crosslinked beads can absorb on the order of 5-50 times their weight in water. The crosslinking can range from 0.5% to 12% in density. Thus, it is desirable to provide a bead whose composition after it has been exposed to water is less than 10% than the combined weight of the bead with the water absorbed therein.

In order to prevent water absorbed by the beads from being lost too rapidly a humectant is added in accordance with the present invention. The humectant can be in the form of glycerin or a deliquescent salt such as calcium sulfate, lithium chloride or potassium acetate. Such humectants retain water in their composition in that they absorb water from the air. Within normal ranges of humidities, such humectants will always have a certain amount of water attached to them. Glycerin, for example, can absorb up to 20% of its weight of water at a relative humidity of 50%. If glycerin is used, it is desirable to, in addition, add a salt such as potassium chloride or sodium chloride to improve conductivity.

A mixture for treating the beads 31 could have the following composition by weight:
Glycerin: 50-80%
Salt: 3-10%
Water: The balance In a representative mixture, BioRad polyacrylamide beads, such as BioGel P100 or P200, whose swollen particle size of 90 microns or less are added to a solution of glycerin, water and salt, as for example 10 grams of glycerin, 10 grams of water and 2 grams of potassium chloride mixed together at room temperature. 15 grams of this solution are added to 1 gram of BioGel P100 beads and intermixed at room temperature and then permitted to sit for a suitable period of time, as for example 10-20 minutes. During this time the crosslinked beads absorbed the glycerin, water and salt mixture to provide a composition of swollen beads to form the vesicle 27 which has a paste-like consistency. The paste-like composition is translucent and is basically colorless. However, it should be appreciated that if desired, dyes can be added to the composition to provide color. The transformation of a bead 31 to a vesicle 27 incorporating the present invention is represented by the diagram shown in FIG. 4. These vesicles 27 form the paste-like composition 19 which can be applied to the surface of the electrode before the electrode is cured so that the vesicles are well intermixed with the surface of the electrode in the manner shown in FIG. 3. Alternatively, the paste-like composition can also be incorporated into the mixture for the electrode 11 so that it is incorporated throughout the matrix of the electrode and before curing the electrode.

When the composition 19 of the present invention is applied to the surface of the electrode, it has been found that there may be a tendency for such a composition to decrease the tackiness of the surface.

It also should be appreciated that the composition of the present invention can be utilized after the composition for the electrode has been cured. Thus, satisfactory results can be achieved either by applying the composition to the surface of the material prior to or after cure. This is particularly true where the surface treatment composition 19 is only applied to a limited surface area of the electrode.

In order not to reduce the tackiness of the electrode, it may be desirable to add a tackifier such as a polymer to the composition to enhance the tackiness of the composition. One such material found to be satisfactory is a polyvinyl pyrrolidone which would have some of its ends protruding beyond the boundaries of the bead and thereby providing a tacky surface which helps to provide a tacky surface and brings the silver-coated fibers 26 into engagement with the skin. A vesicle 36 of this type is illustrated in FIG. 5 in which the fibers 37 protruding from the vesicle are depicted engaging the surface 41 of the dry-electrode material 42. The tackifier can be added to the mixture of glycerin, water and salt hereinbefore described. The tackifier can be a water-soluble polymer with reactive functional groups, for example a vinyl-terminated polymer whose vinyl ends can be made to react with the dry-electrode material and thereby chemically bonding it to the surface of the polymer.

The rather remarkable results which can be achieved by utilizing the composition of the present invention can be seen from FIG. 6 in connection with making ECG measurements with electrodes of the type described in co-pending application, Ser. No. 07/964,917, filed on Oct. 22, 1992. Pairs of electrodes of this type were applied to four different patients and peak-to-peak noise was measured immediately upon placing the electrodes on the patient (which was within approximately 30 seconds) at 1.5 minutes and at 5.5 minutes. The curve 46 represents an uncoated, 1"-diameter, dry electrode in which the surface in contact with the patient was uncoated. It shows that the peak-to-peak noise in millivolts was quite high. It was initially almost one millivolt, and only decreased very slowly to values of slightly above 0.4 millivolts after 5 minutes. In contrast, a 1" diameter electrode represented by curve 48 which had its surface treated with the composition of the present invention exhibited greatly reduced peak-to-peak noise immediately after placement of the electrodes on the skin of the patient Thus, the peak-to-peak noise was only slightly greater than 0.2 millivolt for the 1" electrode, which decreased only slightly to below 0.04 millivolts after 5 minutes. The ECG signal of interest had a value of 2.2 millivolts peak-to-peak. Therefore untreated 1" diameter electrodes had an initial signal-to-noise ratio of 2.2 to 1 and the 1" diameter electrodes treated in accordance with the present invention had an initial signal-to-noise ratio of approximately 10 to 1.

Thus, it can be seen that applying the composition of the present invention to the surface of the electrode has dramatically reduced the initial peak-to-peak noise and increased the signal to noise ratio indicating that the composition of the present invention greatly reduced the resistivity of the skin of the patient to the extent that the resistivity remained at a low value and did not greatly change with time. Thus, a very low signal-to-noise ratio is obtained which is very advantageous in utilizing dry-type electrodes. It makes possible accurate and reliable ECG measurements communicating from the time of application of the electrodes to the skin of the patient. Heretofore, as pointed out previously, it had been necessary to wait a substantial period, as for example as long as 4 minutes before the peak-to-peak noise of an uncoated electrode was reduced to an acceptable value. This is presumably taking place because the moisture of the body released through the skin of the patient gradually improves the conductivity at the skin of the patient. As explained previously, this was an undesirable delay in making accurate ECG measurements and it is for this reason that the present invention represents a significant breakthrough making it possible to make accurate measurements from the commencement of the placement of the electrodes.

What is claimed is:

1. An electrode adapted to be placed in contact with the skin of a patient for reducing the surface resistivity of the skin of the patient, the electrode comprising a member formed of a dry-conductive material and having an outer surface adapted to be placed in contact with the skin of the patient, a composition disposed in at least a portion of the surface of the member, said composition including a plurality of water-containing vesicles.

2. An electrode as in claim 1 wherein the water-containing vesicles are coated on a portion of the outer surface of the electrode.

3. An electrode as in claim 1 wherein said water-containing vesicles are intermixed in the dry conductive material of the member.

4. An electrode as in claim 1 wherein said vesicles are in the form of a crosslinked hydrophilic-type polymer.

5. An electrode as in claim 4 wherein when said vesicles are swollen, the swollen vesicles contain less than 20% by weight of the crosslinked hydrophilic-type polymer.

6. An electrode as in claim 4 wherein the crosslinked polymer has a crosslink density that permits the polymer to swell a maximum of 5–50 times its weight when exposed to pure water.

7. An electrode as in claim 1 wherein said vesicles contain a humectant.

8. An electrode as in claim 7 wherein said humectant is glycerin.

9. An electrode as in claim 8 wherein the vesicles contain a salt.

10. An electrode as in claim 9 wherein said salt is selected from potassium chloride and sodium chloride.

11. An electrode as in claim 7 wherein said humectant is a deliquescent salt.

12. An electrode as in claim 11 wherein said deliquescent salt is potassium acetate.

13. An electrode as in claim 1 wherein the vesicles have a crosslinking density ranging from 0.5%–12%.

14. An electrode as in claim 1 wherein said vesicles incorporate a tackifier.

15. An electrode as in claim 14 wherein said tackifier is in the form of a water-soluble polymer.

16. An electrode as in claim 15 wherein said water-soluble polymer is provided with a reactive functional group.

17. An electrode as in claim 1 wherein said vesicles form a paste.

18. In a composition for the treatment of an electrode adapted to be placed in contact with the skin of the patient for reducing the surface resistivity of the skin of the patient, a plurality of beads formed of a crosslinked hydrophilic polymer, said beads having absorbed therein a mixture increasing the size of the beads from 5–50 times its original size, the mixture being comprised of a humectant and water.

19. A composition as in claim 18 wherein said humectant is glycerin.

20. A composition as in claim 19 wherein said composition includes a salt.

21. A composition as in claim 18 wherein said humectant is a deliquescent salt.

22. A composition as in claim 18 wherein said mixture includes a tackifier.

23. A composition as in claim 22 wherein said tackifier is a water-soluble polymer.

24. A composition as in claim 18 which said mixture has a consistency of paste.

25. In a method for providing a composition for the treatment of an electrode for reducing surface resistivity, providing a batch of crosslinked hydrophilic polymer-type beads having a size less than 90 microns, adding to the beads a mixture of a humectant and water, permitting the beads to absorb the mixture and expand in size to provide a composition having a consistency of paste.

26. A method as in claim 25 together with the step of adding glycerin as a humectant and adding a salt to the mixture.

27. A method as in claim 25 together with the step of adding a deliquescent salt as a humectant to the mixture.

28. A method as in claim 25 together with the step of adding a tackifier to the mixture.

* * * * *